(12) United States Patent
Yamaguchi et al.

(10) Patent No.: US 7,142,305 B2
(45) Date of Patent: Nov. 28, 2006

(54) MICROCHEMICAL SYSTEM

(75) Inventors: Jun Yamaguchi, Tokyo (JP); Akihiko Hattori, Tokyo (JP)

(73) Assignee: Nippon Sheet Glass Company, Limited, Tokyo (JP)

( * ) Notice: Subject to any disclaimer, the term of this patent is extended or adjusted under 35 U.S.C. 154(b) by 0 days.

(21) Appl. No.: 11/090,369

(22) Filed: Mar. 25, 2005

(65) Prior Publication Data

US 2005/0219539 A1      Oct. 6, 2005

Related U.S. Application Data

(63) Continuation of application No. PCT/JP03/11519, filed on Sep. 9, 2003.

(30) Foreign Application Priority Data

Sep. 27, 2002 (JP) ............................. 2002-284152

(51) Int. Cl.
    *G01N 21/00* (2006.01)
(52) U.S. Cl. ........................................ 356/432; 356/442
(58) Field of Classification Search ........ 356/432–442, 356/317, 319, 430; 359/288, 244, 289, 299, 359/350
    See application file for complete search history.

(56) References Cited

U.S. PATENT DOCUMENTS

| | | | | |
|---|---|---|---|---|
| 4,927,268 A * | 5/1990 | Carr et al. | ............... | 356/336 |
| 4,936,674 A * | 6/1990 | Ikeda et al. | ............... | 356/39 |
| 5,155,549 A * | 10/1992 | Dhadwal | ............... | 356/336 |
| 5,513,006 A * | 4/1996 | Schulz et al. | ............... | 356/432 |
| 5,599,502 A | 2/1997 | Miyazaki et al. | | |
| 6,930,778 B1 * | 8/2005 | Yamaguchi et al. | ........ | 356/432 |
| 6,941,041 B1 * | 9/2005 | Yamaguchi et al. | .......... | 385/34 |
| 2003/0223070 A1 * | 12/2003 | Yamaguchi et al. | ........ | 356/432 |
| 2004/0175297 A1 * | 9/2004 | Yamaguchi et al. | ..... | 422/82.05 |

(Continued)

FOREIGN PATENT DOCUMENTS

EP        1 087 223 A1        3/2001

(Continued)

OTHER PUBLICATIONS

Sung-ho Kim: "Diode-Laser-Based Portable Thermal Lensing Spectroscopy System with Optical Fiber", Bulletin of the Korean. Chemical Society, Jan. 20, 1997, vol. 18, No. 1, pp. 108 to 109.

(Continued)

*Primary Examiner*—Hoa Q. Pham
(74) *Attorney, Agent, or Firm*—Frishauf, Holtz, Goodman & Chick, P.C.

(57) ABSTRACT

There is provided a microchemical system which dispenses with the optical axis alignment and positioning of the focal point of the detecting light and that of the exciting light, and is capable of carrying out measurement with high sensitivity. The microchemical system includes a channel-formed plate-shaped member containing a sample, an exciting light source that irradiates exciting light onto the sample via a converging lens, a detecting light source that irradiates detecting light onto a thermal lens formed within the sample by the irradiated exciting light, via the converging lens, and detecting means for detecting the irradiated detecting light via the formed thermal lens. The exciting light source and the detecting light source are connected to the converging lens via an optical fiber for propagating the exciting light and the detecting light to the converging lens. The converging lens is fixed to the channel-formed plate-shaped member, and the optical fiber has a joint part capable of disconnecting the exciting light source and the detecting light source from the converging lens.

20 Claims, 8 Drawing Sheets

U.S. PATENT DOCUMENTS

| | | | |
|---|---|---|---|
| 2004/0196466 A1* | 10/2004 | Yamaguchi et al. | 356/432 |
| 2004/0233449 A1* | 11/2004 | Yamaguchi et al. | 356/432 |
| 2004/0233450 A1* | 11/2004 | Yamaguchi et al. | 356/432 |
| 2004/0257575 A1* | 12/2004 | Yamaguchi et al. | 356/432 |
| 2005/0259259 A1* | 11/2005 | Yamaguchi et al. | 356/432 |
| 2006/0109465 A1* | 5/2006 | Fukuzawa et al. | 356/417 |

FOREIGN PATENT DOCUMENTS

| | | |
|---|---|---|
| JP | 08-178897 A | 7/1996 |
| JP | 10-232210 A | 9/1998 |
| JP | 2001-059829 A | 3/2001 |
| WO | WO 01/55706 A1 | 8/2001 |
| WO | WO 02/40981 A1 | 5/2002 |
| WO | WO 03/010527 A1 | 2/2003 |
| WO | WO 03/036279 A1 | 5/2003 |

OTHER PUBLICATIONS

Jun Yamaguchi, Akihiko Hattori, Manabu Tokeshi and Takehiko Kitamori, "WDM-gata Gohaki o Riyo shita Netsu Lens Kenbikyo no Kogataka", Dai 6 Kai Kagaku to Micro Nano System Kenyukai Keon Yokoshu, Aug. 6, 2002, 6p07, p. 29.

* cited by examiner

MICROCHEMICAL SYSTEM

This application is a Continuation U.S. Application of International Application PCT/JP2003/011519 filed Sep. 9, 2003, which claims priority of Japanese Patent Application No. 2002-284152 filed Sep. 27, 2002.

TECHNICAL FIELD

The present invention relates to a microchemical system.

BACKGROUND ART

In view of the rapidity of chemical reactions, the need to carry out reactions using very small amounts of a sample, on-site analysis, and so on, integration technology for carrying out chemical reactions in very small spaces has attracted attention from hitherto, and research has been carried out with vigor throughout the world.

So-called microchemical systems are one example of such integration technology. Microchemical systems are systems for carrying out mixing, reaction, separation, extraction, detection or the like on a liquid-borne sample in a very fine channel formed in a small glass substrate or the like. Examples of reactions carried out in such a microchemical system include diazotization reactions, nitration reactions, and antigen-antibody reactions. Moreover, examples of extraction/separation include solvent extraction, electrophoretic separation, and column separation. A microchemical system may be used with a single function, for example for only separation, or may be used with a combination of a plurality of functions.

As an example of a microchemical system for only separation out of the above functions, an electrophoresis apparatus for analyzing extremely small amounts of proteins, nucleic acids or the like has been proposed (see, for example, Japanese Laid-Open Patent Publication (Kokai) No. H08-178897). This electrophoresis apparatus has a channel-formed plate-shaped member comprised of two glass substrates joined together. Because the member is plate-shaped, breakage is less likely to occur than in the case of a glass capillary tube having a circular or rectangular cross section, and hence handling is easier.

In these microchemical systems, because the amount of the liquid-borne sample is very small, a highly sensitive detection method is essential. As such a method, a photothermal conversion spectroscopic analysis method that uses a thermal lens effect arising upon a liquid-borne sample in a very fine channel absorbing light has been established. This photothermal conversion spectroscopic analysis method uses a photothermal conversion effect in which light is convergently irradiated onto a liquid-borne sample, whereupon the liquid-borne sample absorbs the light and hence thermal energy is released, and thus the temperature of the solvent is locally raised by this thermal energy, whereby the refractive index thereof changes, and hence a thermal lens is formed. This photothermal conversion spectroscopic analysis method has opened up a path for realizing microchemical systems.

FIG. 5 is a view useful in explaining the principle of a thermal lens.

In FIG. 5, exciting light is convergently irradiated onto an extremely small amount of a liquid-borne sample via an objective lens of a microscope, whereby a photothermal conversion effect is brought about. For most substances, the refractive index drops as the temperature rises, and hence in the liquid containing the liquid-borne sample onto which the exciting light has been convergently irradiated, the refractive index drops, with the drop being larger the closer to the center of the converged light, which is where the rise in temperature is largest. In other words, the refractive index relatively increases with distance from the center of the converged light. This is because the rise in temperature becomes smaller with distance from the center of the converged light due to thermal diffusion. Optically, the resulting refractive index distribution produces the same effect as a concave lens, and hence the effect is referred to as the thermal lens effect. The size of the thermal lens effect, i.e. the power of the concave lens, is proportional to the optical absorbance of the liquid-borne sample. Moreover, in the case that the refractive index increases with temperature, the change in the refractive index is reversed, and hence a thermal lens effect that produces the same effect as a convex lens arises.

In the photothermal conversion spectroscopic analysis method described above, changes in the refractive index of the liquid (sample solution) containing the liquid-borne sample due to thermal diffusion in the liquid are thus observed, and hence the method is suitable for detecting the concentrations of extremely small samples in a liquid.

In the conventional photothermal conversion spectroscopic analysis apparatus, a channel-formed plate-shaped member is disposed below the objective lens of a microscope, and exciting light of a predetermined wavelength outputted from an exciting light source is introduced into the microscope. The exciting light is thus convergently irradiated via the objective lens of the microscope onto a liquid-borne sample in the channel of the channel-formed plate-shaped member. The focal position of the convergently irradiated exciting light is made to be in the sample solution, and hence a thermal lens is formed centered on this focal position.

On the other hand, detecting light having a wavelength different to that of the exciting light is outputted from a detecting light source, and is introduced into the microscope. The detecting light passes through and exits from the microscope, and is thus convergently irradiated onto the thermal lens that has been formed in the sample solution by the exciting light, and passes through the sample solution and is thus diverged or converged. The diverged or converged detecting light exiting from the sample solution forms signal light. The signal light passes through a converging lens and a filter, or just a filter, and is then detected by a detector. The intensity of the detected signal light depends on the thermal lens formed in the sample solution. Note also that alternatively the detecting light may have the same wavelength as the exciting light, or the exciting light may also be used as the detecting light.

In the photothermal conversion spectroscopic analysis apparatus described above, a thermal lens is thus formed in the focal position of the exciting light, and changes in the refractive index of the thermal lens formed are detected using detecting light that has either the same wavelength as the exciting light or a different wavelength thereto (see e.g. Japanese Laid-Open Patent Publication (Kokai) No. H10-232210).

However, with such a photothermal conversion spectroscopic analysis apparatus, the optical systems and so on for the light sources, the measurement section and the detection section (photoelectric conversion section) are complicated in system configuration, and hence such an apparatus has been large in size, and has thus lacked portability. Consequently, there is a problem that there are limitations with regard to the installation site and the operation of the photothermal conversion spectroscopic analysis apparatus.

Moreover, in the photothermal conversion spectroscopic analysis apparatus, the exciting light and the detecting light are led to the liquid-borne sample through open space, and hence various optical system components such as the light sources, mirrors and lenses must be prevented from moving during measurement, and thus a sturdy surface plate for fixing these components is required. Furthermore, the optical axes of the exciting light and the detecting light may shift out of alignment upon changes in the environment such as changes in the temperature, and hence jigs for adjusting for such shifts are required. These jigs are also a cause of the photothermal conversion spectroscopic analysis apparatus becoming larger in size and hence lacking portability.

Moreover, in a microchemical system that uses the photothermal conversion spectroscopic analysis method, in many cases it is necessary for the focal position of the exciting light and the focal position of the detecting light to be different from one another.

FIGS. 6A and 6B are views useful in explaining the formation position of a thermal lens and the focal position of detecting light in the direction of travel of exciting light; FIG. 6A shows a case in which an objective lens has chromatic aberration, and FIG. 6B shows a case in which the objective lens does not have chromatic aberration.

In the case that the objective lens 500 has chromatic aberration, as shown in FIG. 6A, the thermal lens 501 is formed at the focal position 502 of the exciting light, and the focal position 503 of the detecting light is in a position shifted by an amount ΔL from the focal position 502 of the exciting light, so that the detecting light enables changes in the refractive index of the thermal lens 501 to be detected as changes in the focal distance of the detecting light. On the other hand, in the case that the objective lens 500 does not have chromatic aberration, as shown in FIG. 6B, the focal position 503 of the detecting light is almost exactly the same as the position of the thermal lens 501 formed at the focal position 502 of the exciting light. As a result, the detecting light is not deflected by the thermal lens 501, and hence changes in the refractive index of the thermal lens 501 cannot be detected.

However, the objective lens of a microscope is generally manufactured so as not to have chromatic aberration, and hence for the reason described above, the focal position 503 of the detecting light is almost exactly the same as the position of the thermal lens 501 formed at the focal position of the exciting light (FIG. 6B). Changes in the refractive index of the thermal lens 501 thus cannot be detected. There is thus a problem that the position of the liquid-borne sample in which the thermal lens 501 is formed must be shifted from the focal position 503 of the detecting light every time measurement is carried out as shown in FIG. 7A or 7B, or else the detecting light must be diverged or converged slightly using a lens (not shown) before being introduced into the objective lens 500 so that the focal position 503 of the detecting light is shifted from the thermal lens 501 as shown in FIG. 8; consequently, the working efficiency of the user is poor.

It is an object of the present invention to provide a microchemical system which dispenses with the optical axis alignment and positioning of the focal point of the detecting light and that of the exciting light, and is capable of carrying out measurement with high sensitivity.

DISCLOSURE OF THE INVENTION

To attain the above object, in a first aspect of the present invention, there is provided a microchemical system including a channel-formed plate-shaped member that is equipped with a channel for containing a sample, an exciting light source that irradiates exciting light onto the sample via a converging lens, a detecting light source that irradiates detecting light onto a thermal lens formed within the sample by the irradiated exciting light, via the converging lens, and detecting means for detecting the irradiated detecting light via the formed thermal lens, wherein the exciting light source and the detecting light source are connected to the converging lens via an optical fiber for propagating the exciting light and the detecting light to the converging lens, characterized in that the converging lens is fixed to the channel-formed plate-shaped member, and the optical fiber has a joint part capable of disconnecting the exciting light source and the detecting light source from the converging lens.

According to the first aspect of the present invention, the optical fiber can be removably connected using the joint part. Therefore, in the cases of the channel having been stained, the channel-formed plate-shaped member having been broken, and the optical fiber having been broken, by replacing only the channel-formed plate-shaped member to which the converging lens is fixed, it is possible to perform fine and precise detection by suppressing contamination of a liquid-borne sample and reduce the running cost of the microchemical system.

Preferably, the joint part is a connector provided midway of the optical fiber.

With this, the exciting light source and the detecting light source can be easily connected to and disconnected from the converging lens.

More preferably, the joint part is an FC connector.

With this, the exciting light source and the detecting light source can be easily connected to and disconnected from the converging lens. Further, the connection can be made solid, and hence there is less loss in the amount of the exciting light and the detecting light propagating through the optical fiber.

Also preferably, the joint part is provided at an end of the optical fiber via which the optical fiber is connected to the converging lens.

With this, the construction of the joint part can be made simple, whereby the microchemical system can be made smaller in size.

More preferably, the joint part can be removably attached to the converging lens.

With this, the construction of the joint part can be made yet simpler, whereby the microchemical system can be made yet smaller in size.

Further preferably, the joint part comprises an annular member that can be fitted on the converging lens.

With this, the construction of the joint part can be made yet simpler, whereby the microchemical system can be made yet smaller in size.

Also, more preferably, the joint part can be removably attached to the channel-formed plate-shaped member.

With this, the construction of the joint part can be made yet simpler, whereby the microchemical system can be made yet smaller in size.

More preferably, the joint part comprises a first annular member that can be fitted on the converging lens, a second annular member that is fixed to the first annular member in a manner coaxially accommodating the first annular member therein and has an annular protruding part formed on an inner peripheral surface thereof, and a third annular member that is fixed to the channel-formed plate-shaped member in a manner coaxially accommodating the converging lens therein and has an annular groove formed in an outer peripheral surface thereof, for receiving the annular protruding part.

With this, the construction of the joint part can be made yet simpler, whereby the microchemical system can be made yet smaller in size.

Also, further preferably, the joint part comprises pins erected at symmetrical locations with respect to the converging lens, and an annular member that is coaxially fixed to the optical fiber and has holes formed in an end face thereof which is opposed to the channel-formed plate-shaped member.

With this, the construction of the joint part can be made yet simpler, whereby the microchemical system can be made yet smaller in size.

Also preferably, the joint part enables connection between the exciting light source and the detecting light source, and the converging lens, in a manner such that the optical axis of the converging lens and the optical axis of the optical fiber are coaxial with each other.

With this, jigs for aligning the optical axes of the exciting light and the detecting light are made unnecessary, so that the construction of the joint part can be made yet simpler, whereby the microchemical system can be made yet smaller in size.

Also preferably, the frequency of the exciting light is different from that of the detecting light.

With this, the focal positions of the exciting light and the detecting light can be shifted from one another without using any external optical systems, whereby the microchemical system can be made yet smaller in size.

Also preferably, the converging lens has chromatic aberration.

With this, the focal positions of the exciting light and the detecting light can be positively shifted from one another without using any external optical systems.

Also preferably, the converging lens is a gradient index lens.

With this, the converging lens can be made smaller in size, whereby the microchemical system can be made yet smaller in size.

More preferably, the gradient index lens is a rod lens having a cylindrical shape.

With this, the gradient index lens can be easily held, and the optical axes of the optical fiber and that of the gradient index lens can be easily aligned with each other.

Also preferably, the channel-shaped plate-formed member is made of a glass.

With this, the channel-shaped plate-formed member has high resistance to chemicals, whereby the detecting accuracy of the microchemical system can be improved.

Also preferably, the optical fiber propagates the exciting light and the detecting light to the converging lens with a single mode.

With this, the thermal lens formed by the exciting light can be made smaller in size with little aberration, and hence the detecting accuracy of the microchemical system can be improved.

Also preferably, the detecting means is fixed on a surface of the channel-formed plate-shaped member, opposite to the converging lens fixed thereto, at a location facing toward the channel of the channel-formed plate-shaped member.

With this, the adjustment of the positions of the converging lens and the detecting means are made unnecessary, and moreover, since jigs for the adjustment are unnecessary, the microchemical system can be made yet smaller in size, and further the positioning of the converging lens and the detecting means with respect to the channel can be more reliably carried out whenever analysis of a sample is to be carried out, whereby the microchemical system can perform detection with enhanced reproducibility and increased precision.

BRIEF DESCRIPTION OF THE DRAWINGS

FIGS. 6A and 6B are views useful in explaining the formation position of a thermal lens and the focal position of detecting light with respect to the direction along the optical axis of exciting light, in which:

FIG. 6A shows a case in which an objective lens has chromatic aberration; and FIG. 6B shows a case in which the objective lens does not have chromatic aberration;

FIGS. 7A and 7B are views useful in explaining the formation position of a thermal lens and the focal position of the detecting light with respect to the optical axis of the exciting light, in which:

FIG. 7A shows a case in which the thermal lens is formed closer to the objective lens than is the focal position of the detecting light; and FIG. 7B shows a case in which the thermal lens is formed in a position further from the objective lens than is the focal position of the detecting light.

BEST MODE FOR CARRYING OUT THE INVENTION

Hereafter, embodiments of the present invention will now be described in detail with reference to the drawings.

Figure 1:
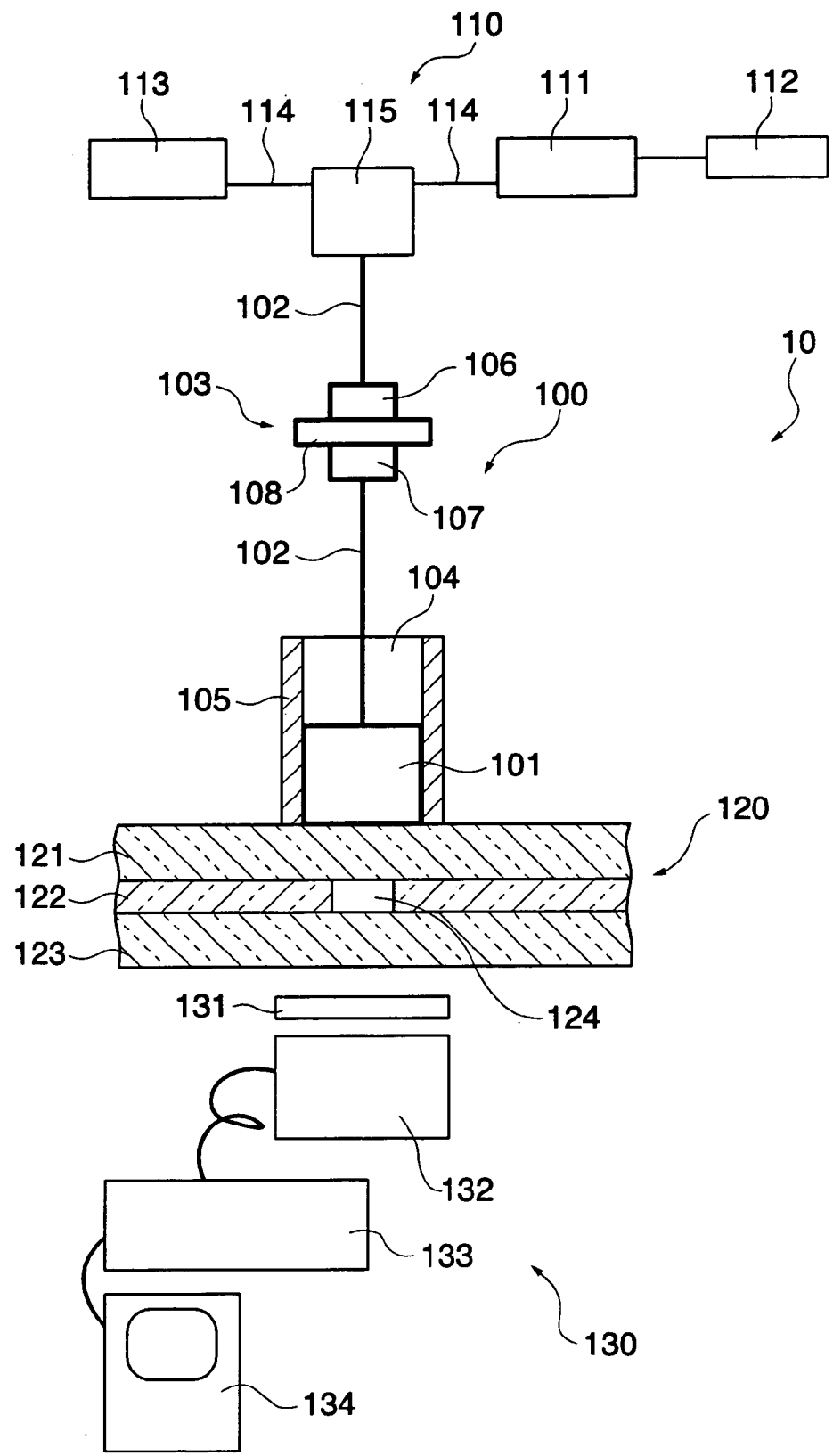
FIG. 1 is a view schematically showing the construction of a microchemical system according to a first embodiment of the present invention.

FIG. 1 is a view schematically showing the construction of a microchemical system according to a first embodiment of the present invention.

In FIG. 1, the microchemical system 10 is comprised of a channel-formed plate-shaped member 120 that has a channel filled with a liquid-borne sample, a lens-equipped optical fiber 100 that is disposed above the channel-formed plate-shaped member 120 and has a lens fitted at an end thereof, a light source unit 110 that is connected to the lens-equipped optical fiber 100, for irradiating, via the lens-quipped optical fiber 100, exciting light onto the liquid-borne sample in the channel of the channel-formed plate-shaped member 120, and detecting light to a thermal lens formed in the liquid-borne sample by the exciting light, and a detecting device 130 that is disposed below the channel-formed plate-shaped member 120, for detecting the detecting light via the thermal lens formed in the sample liquid in the channel of the channel-formed plate-shaped member 120 by the exciting light.

The channel-formed plate-shaped member 120 is comprised of an upper glass substrate 121, a middle glass substrate 122, and a lower glass substrate 123, which are sequentially stacked in the mentioned order from the lens-equipped optical fiber 100 side, and joined together by an adhesive.

The middle glass substrate 122 as the middle layer of the channel-formed plate-shaped member 120 has a channel 124 formed therein through which the sample liquid is passed when the microchemical system 10 carries out mixing, agitation, synthesis, separation, extraction, detection or the like operation, on the sample liquid.

From the perspective of durability and chemical resistance, the material of the upper glass substrate 121, the middle substrate glass 122, and the lower glass substrate 123 of the channel-formed plate-shaped member 120 is preferably a glass. In particular, considering usage with biological samples such as cell samples, for example in DNA analysis, a glass having high acid resistance and alkali resistance is preferable, specifically a borosilicate glass, a soda lime glass, an aluminoborosilicate glass, a quartz glass or the like. However, if the usage is limited accordingly, then a channel-formed plate-shaped member 120 manufactured using an organic material such as a plastic may be used instead.

Examples of adhesives that can be used to bond the upper glass substrate 121, the middle glass substrate 122, and the lower glass substrate 123 together include organic adhesives, such as ultraviolet-curing type adhesives, thermosetting type adhesives, two-liquid-curing type acrylic adhesives, and epoxy adhesives, and inorganic adhesives. Alternatively, the upper glass substrate 121, the middle glass substrate 122, and the lower glass substrate 123 may be fused together by heat fusion.

The lens-equipped optical fiber 100 is comprised of a gradient index rod lens 101 having a transparent cylindrical shape, an optical fiber 102 connected to the light source unit 110, for propagating the exciting light and the detecting light with a single mode, an annular member 105 fixed to an end of the optical fiber 102 via a ferrule 104, for having the gradient index rod lens 101 fitted therein for fixing the same thereto, and an FC connector 103 (joint part) disposed midway of the optical fiber 102.

The ferrule 104 has a cylindrical shape with the same outside diameter as that of the gradient index rod lens 101 for making the outside diameter of the optical fiber 102 be the same as that of the rod lens 101, and has the optical fiber 102 inserted therethrough. The ferrule 104 is placed on one surface of the gradient index rod lens 101 and fixed to the gradient index rod lens 101 by the annular member 105 as described above.

The optical fiber 102 may be fixed in intimate contact with the gradient index rod lens 101 or may be fixed via the ferrule 104 in a manner spaced from the gradient index rod lens 101.

The gradient index rod lens 101 has an exit-side surface thereof opposite to the ferrule 104 fixed to a side surface of the upper glass substrate 121 opposite to the middle glass substrate 122 such that a multiplex of exciting light and detecting light exiting from the gradient index rod lens 101 is perpendicularly incident on the channel-formed plate-shaped member 120 to enter the channel 124

The gradient index rod lens 101 may be fixed to the upper glass substrate 121 directly using an adhesive, or using a predetermined jig. Examples of the adhesives for fixing the gradient index rod lens 101 to the upper glass substrate 121 include organic adhesives, such as acrylic adhesives including ultraviolet-curing type adhesives, thermosetting adhesives, and two-liquid-curing type adhesives, and epoxy adhesives, and inorganic adhesives.

The gradient index rod lens 101 is set such that the focal position of the detecting light is shifted slightly by an amount ΔL relative to the focal position of the exciting light.

The value ΔL varies according to the thickness of the liquid-borne sample on which measurements are to be carried out. Assuming that a confocal length is represented by Ic, when carrying out measurements on a liquid-borne sample having a thickness lower than the confocal length, it is most preferable for ΔL to be equal to $\sqrt{3} \times Ic$.

The confocal length Ic (nm) is given by $Ic = \pi \times (d/2)^2 / \lambda_1$. Here, d represents an airy disk and is given by $d = 1.22 \times \lambda_1 / NA$, $\lambda_1$ represents the wavelength (nm) of the exciting light, and NA represents the numerical aperture of the gradient index rod lens 101. In the case of using the optical fiber 102, the numerical aperture of the light exiting from the optical fiber 102 is small, and hence it is necessary to use the numerical aperture of the optical fiber 102 in the calculation of the confocal length when using a rod lens having a large numerical aperture.

The value ΔL represents the difference between the focal position of the detecting light and the focal position of the exciting light, and hence the result is the same regardless of whether the focal distance of the detecting light is longer or shorter than the focal distance of the exciting light.

The gradient index rod lens 101 is configured such that the refractive index changes continuously in a radial direction from the position of a central axis thereof that extends in a longitudinal direction thereof. Such a rod lens is known as a converging light-transmitting body configured such that the refractive index n(r) at a position a distance r in the radial direction from the central axis is given approximately by the quadratic equation in r, $$n(r) n_0 \{1 - (g^2/2) \times r^2\},$$

wherein $n_0$ represents the refractive index at the central axis, and g represents a quadratic distribution constant.

If the length $z_0$ of the gradient index rod lens 101 is chosen to be in a range of $0 < z_0 < \pi/2g$, then even though the gradient index rod lens 101 has flat end faces, the gradient index rod lens 101 will have the same image formation characteristics as an ordinary convex lens; when a parallel light beam is incident on the gradient index rod lens 101, a focal point will be formed by the parallel incident light beam at a position a distance $s_0$ from the exit-side end of the gradient index rod lens 101, where $$s_0 = \cot(g z_0) / n_0 g.$$

Such a gradient index rod lens 101 may be manufactured, for example, using the following method.

A rod is formed from a glass having as principal components thereof 57 to 63 mol % of $SiO_2$, 17 to 23 mol % of $B_2O_3$, 5 to 17 mol % of $Na_2O$, and 3 to 15 mol % of $Tl_2O$, and then the glass rod is treated in an ion exchange medium such as potassium nitrate, thus carrying out ion exchange between thallium ions and sodium ions in the glass and potassium ions in the ion exchange medium, and hence producing a refractive index distribution in the glass rod in which the refractive index decreases continuously from the central axis of the glass rod radially outward.

Because the surface of the gradient index rod lens 101 is flat, it can be easily attached to the end of the optical fiber 102, and moreover the optical axis of the gradient index rod lens 101 and the optical axis of the optical fiber 102 can easily be aligned with one another.

The gradient index rod lens 101 is connected to one end of the optical fiber 102 that propagates the exciting light and the detecting light; as a result, there is no need to adjust the optical axes of the exciting light and the detecting light and the optical axis of the gradient index rod lens 101 each time measurement is carried out, and moreover jigs for aligning the optical axes and a predetermined sturdy surface plate are unnecessary, and hence the working efficiency of a user can be improved, and moreover the microchemical system can be made smaller in size.

The FC connector 103 is comprised of FC plugs 106 and 107, and an adapter 108 having the FC plugs 106 and 107 removably connected thereto. The FC plugs 106 and 107 are each comprised of a cylindrical ferrule having the optical fiber 102 connected along the central axis thereof and having a diameter of 2.5 mm, and a nut coaxially and rotatably receiving the ferrule therein. The adapter 108 is comprised of a cylindrical flange, and two cylindrical protruding parts coaxially and perpendicularly attached to opposite sides of the flange. The two cylindrical protruding parts have a thread formed on the outer periphery thereof in association with the nuts of the FC plugs 106 and 107. Further, the flange and the two protruding parts are formed therethrough with a through hole coaxial with the flange, for receiving the ferrules of the FC plugs 106 and 107 therein. Further, the FC plugs 106 and 107 and the adapter 108 have a rotation-inhibiting means attached thereto for inhibiting rotation of the ferrules inserted into the through hole of the adapter 108, when the associated nuts are fastened.

The ferrules of the FC plugs 106 and 107 are inserted into the through hole of the adapter 108, and the nuts of the FC plugs 106 and 107 are screwed onto the thread of the adapter 108, whereby the FC plugs 106 and 107 are fastened to the adapter 108 such that the opposed ends of the FC plugs 106 and 107 are brought into contact with each other to establish connection of the optical fibers 102.

By fixing the FC plugs 106 and 107 via the adapter 108 as described above, it is possible to maintain connection of the optical fibers via the ferrules even in a vibrating environment. Further, since the FC plugs 106 and 107 are connected to the adapter 108 using the nuts as describe above, the FC plugs 106 and 107 can be easily attached to and removed from the adapter 108. The durability of the FC connector 103 is guaranteed to 1,000 times of attachment and removal thereof.

The insertion loss of the amounts of the exciting light and the detecting light propagating through the optical fiber 102 caused by provision of the FC connector 103 midway of the optical fiber 102 is as low as 0.3 dB, so that the optical fiber 102 is capable of propagating the exciting light and the detecting light therethrough by way of the FC connector 103 almost without any loss.

When detecting a very small amount of liquid-borne sample using the photothermal conversion spectroscopic analysis method, it is preferable to narrow down the exciting light as much as possible to thereby increase energy thereof used for photothermal conversion, and at the same time form a thermal lens generated by the exciting light such that the thermal lens has little aberration. It is preferable for the optical fiber 102 to propagate the exciting light and the detecting light with a single mode.

Since the optical fiber 102 is used with a single mode, and the light exiting from the optical fiber 102 will always have a Gaussian distribution, the focal point of the exciting light will be small in size. Moreover, in the case that the thermal lens produced by the exciting light is small in size, to make the amount of the detecting light that passes through the thermal lens be as high as possible, it is preferable to also narrow down the detecting light as much as possible. From this standpoint as well, it is preferable for the optical fiber 102 to propagate the exciting light and the detecting light with a single mode.

Any type of optical fiber can be used as the optical fiber 102 insofar as it can transmit the exciting light and the detecting light. However, in the case that a multi-mode optical fiber is used, the exiting light will not have a Gaussian distribution, and moreover the pattern of the exiting light will vary according to various conditions such as the state of curvature of the optical fiber 102, and hence it will not necessarily be possible to obtain stable exiting light. Carrying out measurement on a very small amount of a liquid-borne sample will thus be difficult, and moreover there may be a lack of stability in the measured value. It is thus preferable for the optical fiber 102 to be a single-mode optical fiber as described above.

If the leading end of the optical fiber were processed into a spherical shape or the like to form a lens, then it would be possible to narrow down the exciting light and the detecting light without installing a separate lens at the leading end of the optical fiber. However, in this case, there would be hardly any chromatic aberration, and hence the focal positions of the exciting light and the detecting light would be almost the same as one another. There would thus be a problem of the thermal lens signal being hardly detectable. Moreover, aberration would be high for the lens formed by processing the leading end of the optical fiber, and hence there would also be a problem of the focal points of the exciting light and the detecting light being large. In the first embodiment of the present invention, a gradient index rod lens 101 is thus installed at the leading end of the optical fiber 102.

The light source unit 110 is comprised of an exciting light source 111 that outputs the exciting light, a modulator 112 that is connected to the exciting light source 111 and modulates the exciting light output therefrom, a detecting light source 113 that outputs the detecting light, and a two-wavelength multiplexing device 115 that is connected to the exciting light source 111 and the detecting light source 113 via respective optical fibers 114, and at the same time connected to the optical fiber 102 of the lens-equipped optical fiber 100, for multiplexing the exciting light output from the exciting light source 111 and the detecting light output from the detecting light source 113 to cause the multiplexed light of the exciting light and the detecting light to enter the optical fiber 102.

In the light source unit 110, a dichroic mirror may be used in place of the two-wavelength multiplexing device 115, to multiplex the exciting light output from the exciting light source 111 and the detecting light output from the detecting light source 113 to cause the multiplexed light of the exciting light and the detecting light to enter the optical fiber 102.

The detecting device 130 is comprised of a wavelength filter 131 provided in a position facing toward the channel 124 of the channel-formed plate-shaped member 120 and opposite to the optical fiber 100, for separating the multiplexed exciting light and detecting light and selectively allows only the detecting light to pass therethrough, a photoelectric converter 132 provided in a position under the wavelength filter 131 and facing toward the channel 124, for detecting the detecting light, and a computer 134 connected to the photoelectric converter 132 via a lock-in amplifier 133.

In the detecting device 130, a predetermined member having a pinhole formed therein in order for only part of the detecting light to be selectively transmitted may also be provided in a position upstream of the photoelectric converter 132 in the optical path of the detecting light.

Signals obtained by the photoelectric converter 132 are sent to the lock-in amplifier 133 for carrying out synchronization with the modulator 112 that modulates the exciting light, and are then analyzed by the computer 134.

According to the microchemical system shown in FIG. 1, it is provided with the FC connector 103 equipped with the FC plugs 106 and 107 that can be removably attached midway of the optical fiber 102, and hence it is possible to remove the channel-formed plate-shaped member 120 to which the gradient index rod lens 101 is fixed from the microchemical system 10 by separating the FC plugs 106 and 107 joined together. As a result, in the cases of the inside of the channel 124 of the channel-formed plate-shaped member 120 having been stained, the channel-formed plate-shaped member 120 having been broken, and the gradient index rod lens 101 having been broken, it is only required to replace the channel-formed plate-shaped member 120 alone to which the gradient index rod lens 101 is fixed, and hence it is possible to reduce the running cost of the microchemical system 10 and perform fine and precise measurement by suppressing contamination of the liquid-borne sample caused by replacing the channel-formed plate-shaped member 120 to which the gradient index rod lens 101 is fixed each time a liquid-borne sample for detection is changed, as much as possible.

According to the microchemical system shown in FIG. 1, the gradient index rod lens 101 is fixed to the leading end of the optical fiber 102 that propagates the exciting light and the detecting light and at the same to the surface of the channel-formed plate-shaped member 120 in a manner facing toward the channel 124. As a result, it is not necessary to adjust the optical axes of the exciting light and the detecting light propagating through the optical fiber 102 and that of the gradient index rod lens 101, and in addition, it is not necessary to adjust the positions of the gradient index rod lens 101 and the channel 123. Therefore, it is possible to dispense with predetermined jigs and a predetermined sturdy surface plate for alignment of the optical axes of the exciting light and the detecting light and that of the gradient index rod lens 101 or positioning of the gradient index rod lens 101 and the channel 124 relative to each other, so that it is possible to improve the working efficiency of the user and reduce the size of the microchemical system.

According to the microchemical system 10 shown in FIG. 1, the focal position of the exciting light that has passed through the gradient index rod lens 101 must be in the channel 204 of the channel-formed plate-shaped member 120. The gradient index rod lens 101 is fixed to the upper glass substrate 121 of the channel-formed plate-shaped member 120 in contact therewith, so that the focal length of the exciting light exiting from the gradient index rod lens 101 can be adjusted through the thickness of the upper glass substrate 121. Further, in the case that the thickness of the upper glass substrate 121 is insufficient, a spacer may be inserted between the gradient index rod lens 101 and the upper glass substrate 121 to fix the gradient index rod lens 101 and the upper glass substrate 121 to each other with the spacer interposed therein whereby the focal length can be adjusted. In the case that the focal position of the exciting light is fixed in advance to be in the channel 124 of the channel-formed plate-shaped member 120 in this way, subsequent adjustment of the focal distance becomes unnecessary, and hence the microchemical system can be made yet smaller in size.

Although in the first embodiment of the present invention, the FC connector 103 is provided midway of the optical fiber 102, this is not limitative, but in place of the FC connector 103, there may be used a D-4 style connector, a ST-style connector, an FDDI-MIC connector, and an ESCON connector.

Figure 2:
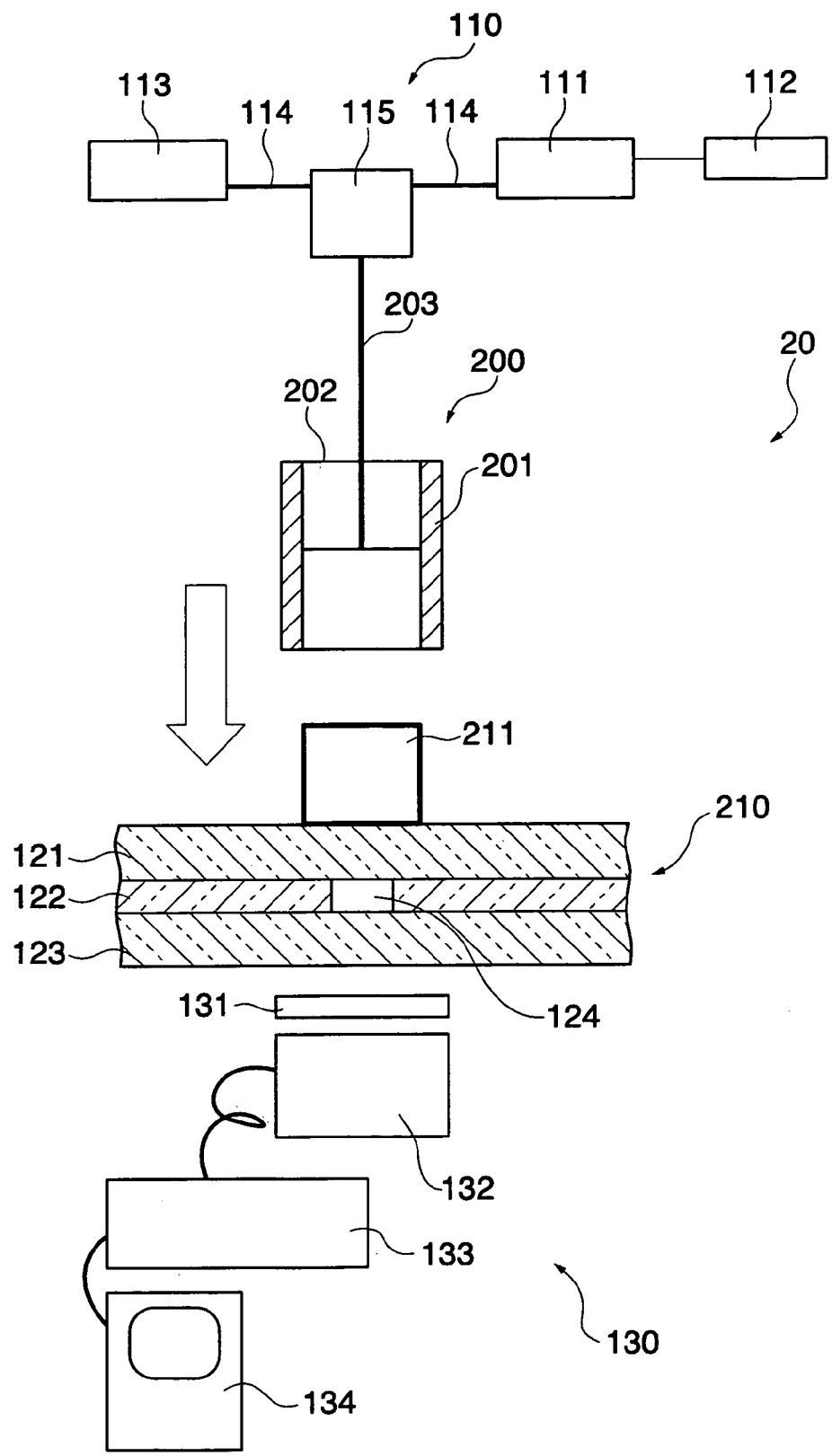
FIG. 2 is a view schematically showing the construction of a microchemical system according to a second embodiment of the present invention.

FIG. 2 is a view schematically showing the construction of a microchemical system according to a second embodiment of the present invention.

In FIG. 2, the microchemical system 20 according to the second embodiment basically has the same construction as that of the microchemical system 10 shown in FIG. 1. Therefore, identical components are represented by the same reference numerals, and duplicate description of these components is omitted. The following description will be given of different components.

In FIG. 2, the microchemical system 20 is distinguished from the microchemical system 10 shown in FIG. 1 in that the lens-equipped optical fiber 100 is replaced by a stopper-equipped optical fiber 200, and the channel-formed plate-shaped member 120 is replaced by a channel-formed plate-shaped member 210.

The channel-formed plate-shaped member 210 is comprised of the channel-formed plate-shaped member 120 appearing in FIG. 1, and a gradient index rod lens 211 having the same shape, the same size, and the same characteristics as those of the gradient index rod lens 101 appearing in FIG. 1. The gradient index rod lens 211 has an exit-side surface thereof fixed to the surface of the upper glass substrate 121 opposite to the middle glass substrate 122 such that the exciting light and the detecting light exiting from the gradient index rod lens are perpendicularly incident on each of the upper glass substrate 121, the middle glass substrate 122, and the lower glass substrate 123 to enter the channel 124.

The stopper-equipped optical fiber 200 is comprised of an optical fiber 203 connected to the two-wavelength multiplexing device 115, and an annular member 201 (joint part) fixed to the leading end of the optical fiber 203 via a ferrule 202, for having the gradient index rod lens 211 fitted therein. The optical fiber 203 has the same characteristics as those of the optical fiber 102 of the microchemical system 10 shown in FIG. 1.

The annular member 201 is formed such that the inner diameter of a cross-section thereof has approximately the same size as the diameter of a cross-section of the gradient index rod lens 211, for being fitted on the gradient index lens 211, whereby the gradient index rod lens 211 can be removably attached thereto by fitting the same in the annular member 201.

According to the microchemical system 20 shown in FIG. 2, by fitting the annular member 201 of the stopper-equipped optical fiber 200 onto the gradient index rod lens 211 of the channel-formed plate-shaped member 210, the optical axes of the exciting light and detecting light that propagate through the optical fiber 203 and the optical axis of the gradient index rod lens 211 can accurately aligned with each other.

According to the microchemical system 20 shown in FIG. 2, the annular member 201 of the stopper-equipped optical fiber 200 can be removably fitted on the gradient index rod lens 211 of the channel-formed plate-shaped member 210. Therefore, in the cases of the inside of the channel 124 of the channel-formed plate-shaped member 210 having been stained, and the channel-formed plate-shaped member 210 having been broken, it is only required to replace the channel-formed plate-shaped member 210 alone to which the gradient index rod lens 211 is fixed, and further it is possible to perform fine and precise measurement by suppressing contamination of the liquid-borne sample caused by replacing the channel-formed plate-shaped member 210 to which the gradient index rod lens 211 is fixed each time a liquid-borne sample for detection is changed, as much as possible.

According to the microchemical system 20 shown in FIG. 2, the gradient index rod lens 211 is fixed to the surface of the upper glass substrate 121 of the channel-formed plate-shaped member 210 in a manner facing toward the channel 124. As a result, it is not necessary to adjust the positions of the gradient index rod lens 211 and the channel 124, and hence it is possible to dispense with predetermined jigs and a predetermined sturdy surface plate for positioning of the gradient index rod lens 211 and the channel 124 relative to each other, so that it is possible to improve the working efficiency of the user and reduce the size of the microchemical system.

Figure 3:
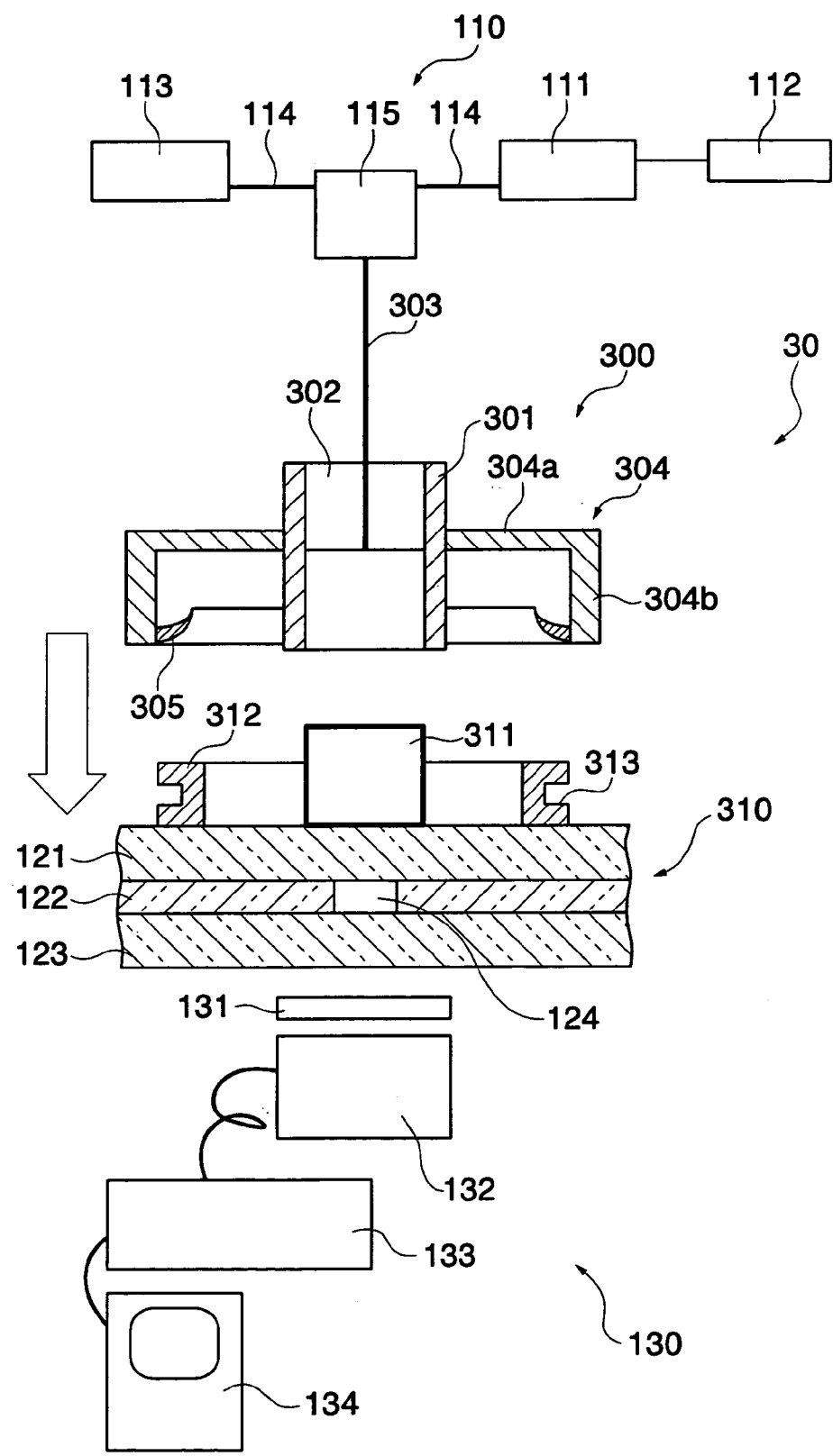
FIG. 3 is a view schematically showing the construction of a microchemical system according to a third embodiment of the present invention.

FIG. 3 is a view schematically showing the construction of a microchemical system according to a third embodiment of the present invention.

In FIG. 3, the microchemical system 30 according to the third embodiment basically has the same construction as that of the microchemical system 10 shown in FIG. 1. Therefore, identical components are represented by the same reference numerals, and duplicate description of these components is omitted. The following description will be given of different components.

In FIG. 3, the microchemical system 30 is distinguished from the microchemical system 10 shown in FIG. 1 in that the lens-equipped optical fiber 100 is replaced by a stopper-equipped optical fiber 300, and the channel-formed plate-shaped member 120 is replaced by a channel-formed plate-shaped member 310.

The channel-formed plate-shaped member 310 is comprised of the channel-formed plate-shaped member 120 appearing in FIG. 1, a gradient index rod lens 311 having the same shape, the same size, and the same characteristics as those of the gradient index rod lens 101 appearing in FIG. 1, and an annular member 312 (third annular member).

The gradient index rod lens 311 has an exit-side surface thereof fixed to the surface of the upper glass substrate 121 opposite to the middle glass substrate 122 such that the exciting light and the detecting light exiting from the gradient index rod lens 311 are perpendicularly incident on each of the upper glass substrate 121, the middle glass substrate 122, and the lower glass substrate 123 to enter the channel 124.

The stopper-equipped optical fiber 300 is comprised of an optical fiber 303 connected to the two-wavelength multiplexing device 115, and an annular member 301 (first annular member) fixed to the leading end of the optical fiber 303 via a ferrule 302, for having the gradient index rod lens 311 fitted therein, and a stopper 304 (second annular member) fitted on the annular member 301. The stopper 304 is comprised of a collar 304a fixed to the annular member 301, and an annular part 304b formed integrally with the periphery of the collar 304a. On an inner peripheral surface of the annular part 304b, there is provided a lip-shaped annular protruding part 305 made of a resilient member, such as rubber.

The annular member 312 is fixed to the upper glass substrate 121 in a manner receiving the gradient index rod lens 311 therein, and has an annular groove 313 formed in the outer peripheral surface thereof, for receiving the annular protruding part 305.

The annular member 301 has a hollow cylindrical shape, and is formed such that the inner diameter of a cross-section thereof has approximately the same size as the diameter of a cross-section of the gradient index rod lens 311, for being fitted on the gradient index lens 311, whereby the gradient index rod lens 311 can be removably attached thereto by fitting the same in the annular member 301.

The stopper-equipped optical fiber 300 is removably integrated with the channel-formed plate-shaped member 310 by having the annular protruding part 305 of the stopper 304 received in the annular groove 313 of the annular member 312 to supportingly embrace the annular groove 313 by the annular protruding part 305, when the annular member 301 is fitted on the gradient index rod lens 311.

According to the microchemical system 30 shown in FIG. 3, when the annular member 301 is fitted on the gradient index rod lens 311, the stopper 3304 is fitted on the annular member 312 such that the annular protruding part 305 of the stopper 304 is received in the annular groove 313 of the annular member 312 to supportingly embrace the annular groove 313. Therefore, by merely fitting the annular member 301 of the stopper-equipped optical fiber 300 on the gradient index rod lens 311 of the channel-formed plate-shaped member 310, it is possible to precisely align the optical axes of the exciting light and the detecting light propagating through the optical fiber 303 with the optical axis of the gradient index rod lens 311, and stably hold the positions of these optical axes for precise measurement.

According to the microchemical system 30 shown in FIG. 3, the annular member 301 of the optical fiber 300 can be removably fitted on the gradient index rod lens 311 of the channel-formed plate-shaped member 310. Therefore, in the cases of the inside of the channel 124 of the channel-formed plate-shaped member 310 having been stained, and the channel-formed plate-shaped member 310 having been broken, it is only required to replace the channel-formed plate-shaped member 310 alone to which the gradient index rod lens 311 is fixed, and further it is possible to perform fine and precise measurement by suppressing contamination of the liquid-borne sample caused by replacing the channel-formed plate-shaped member 310 to which the gradient index rod lens 311 is fixed each time a liquid-borne sample is changed, as much as possible.

According to the microchemical system 30 shown in FIG. 3, the gradient index rod lens 311 is fixed to the surface of the upper glass substrate 121 of the channel-formed plate-shaped member 310 in a manner facing toward the channel 124. As a result, it is not necessary to adjust the positions of the gradient index rod lens 311 and the channel 124, and hence it is possible to dispense with predetermined jigs and a predetermined sturdy surface plate for positioning of the gradient index rod lens 211 and the channel 124 relative to each other, so that it is possible to improve the working efficiency of the user and reduce the size of the microchemical system.

In the microchemical system 30 shown in FIG. 3, the shapes of the stopper 304 and the annular member 312 are not limited to those described above.

Figure 4:
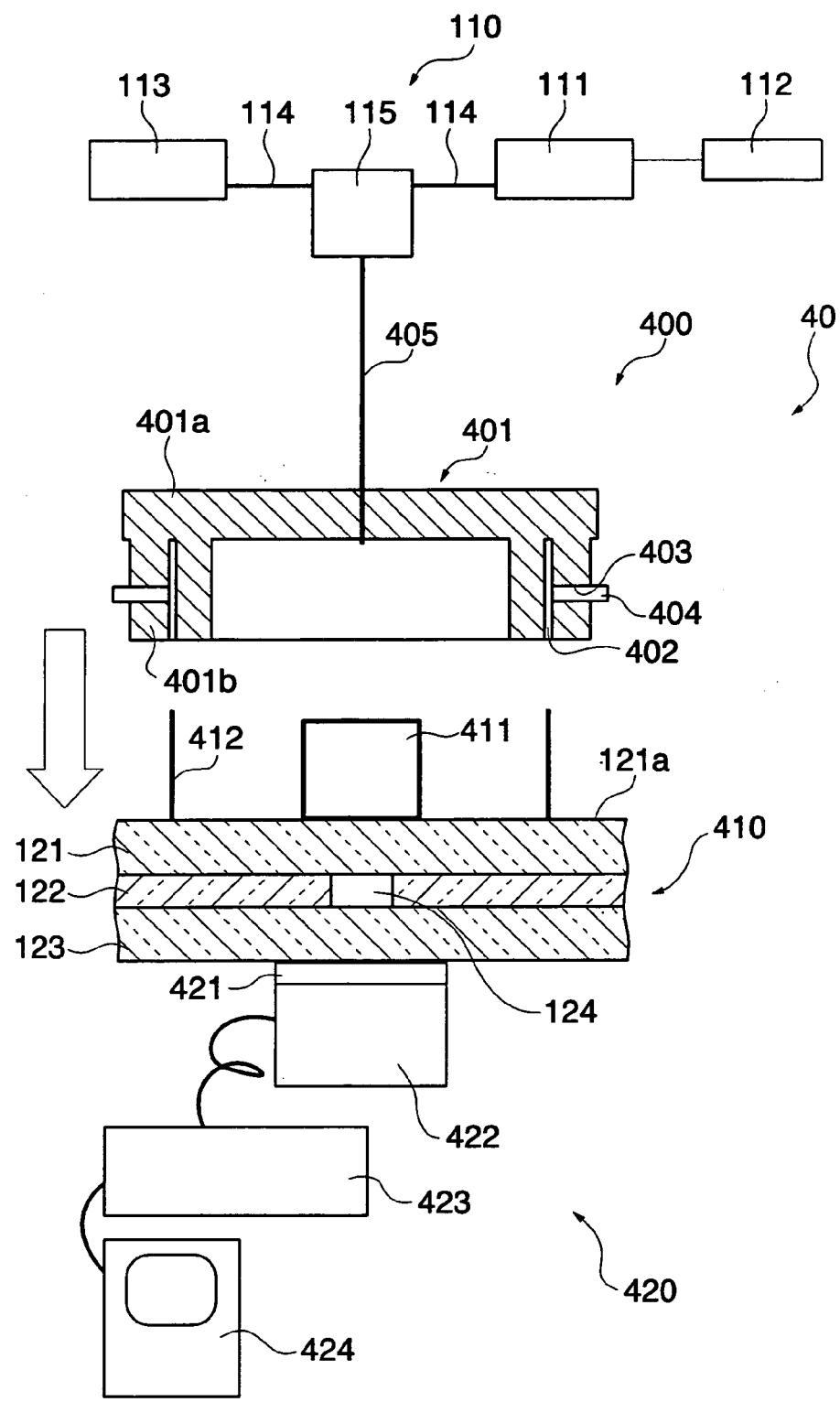
FIG. 4 is a view schematically showing the construction of a microchemical system according to a fourth embodiment of the present invention.
Figure 5:
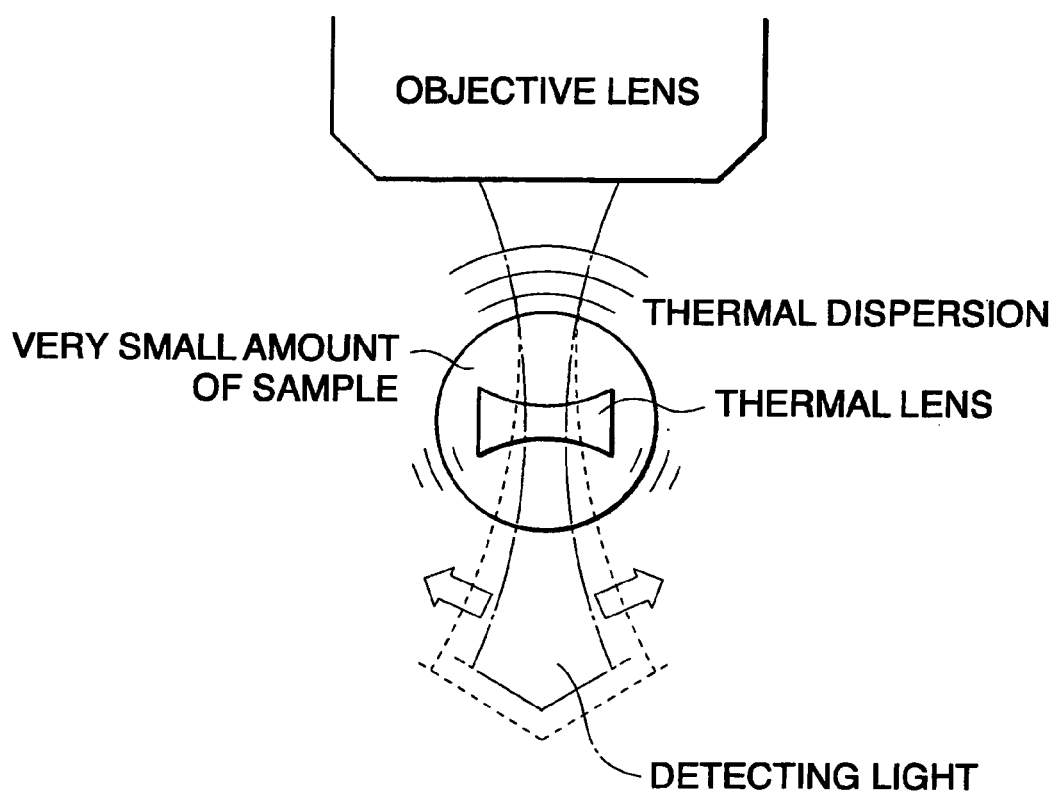
FIG. 5 is a view useful in explaining the principle of a thermal lens.
Figure 6A:
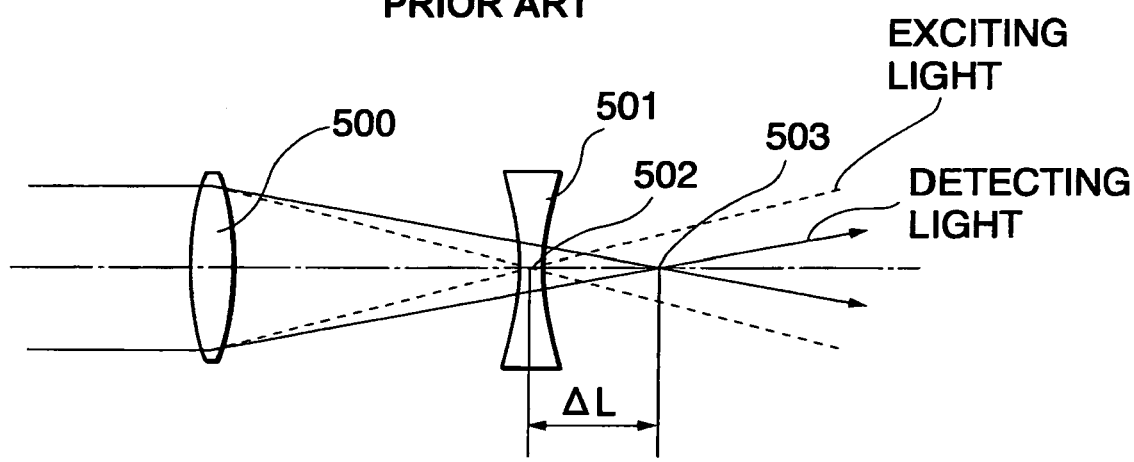
Figure 6B:
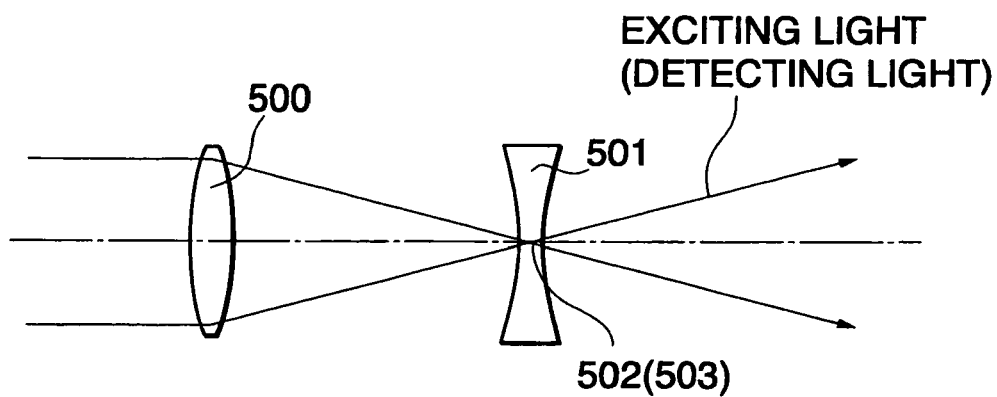
Figure 7A:
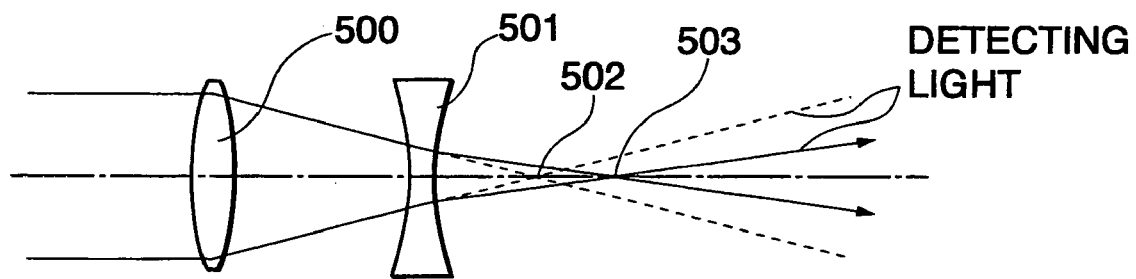
Figure 7B:
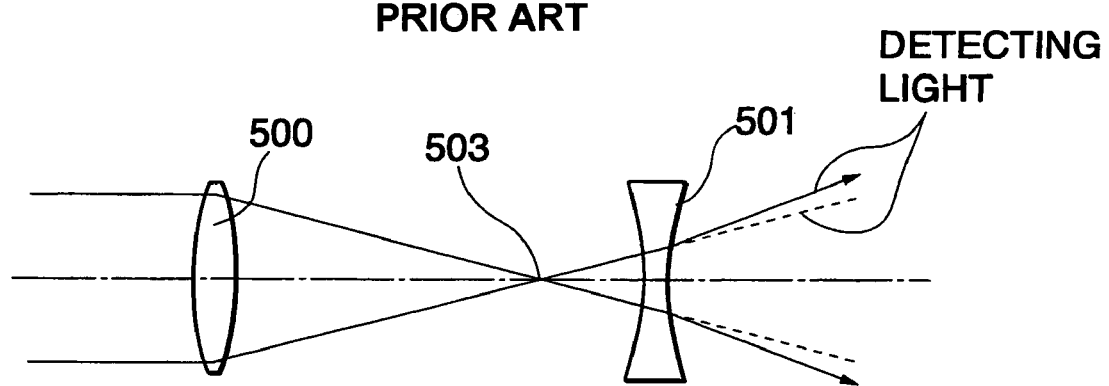
Figure 8:
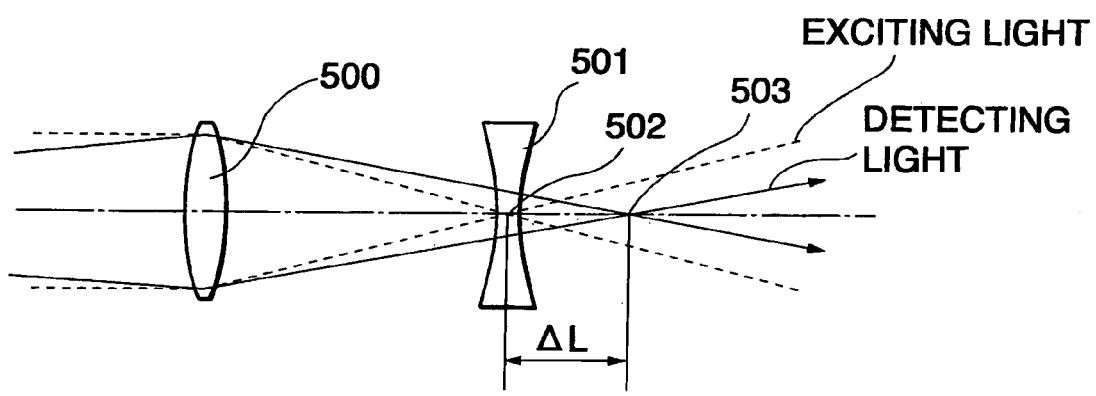
FIG. 8 is a view useful in explaining a method of detecting changes in refractive index of a thermal lens in a conventional photothermal conversion spectroscopic analysis apparatus, and shows a case in which a concave lens is put into an optical path so that detecting light is made into divergent light, and hence the focal position of the detecting light is made to be further away than the focal position of exciting light.

FIG. 4 is a view schematically showing the construction of a microchemical system according to a fourth embodiment of the present invention.

In FIG. 4, the microchemical system 40 according to the fourth embodiment basically has the same construction as that of the microchemical system 10 shown in FIG. 1. Therefore, identical components are represented by the same reference numerals, and duplicate description of these components is omitted. The following description will be given of different components.

In FIG. 4, the microchemical system 40 is distinguished from the microchemical system 10 shown in FIG. 1 in that the lens-equipped optical fiber 100 is replaced by a stopper-equipped optical fiber 400, the channel-formed plate-shaped member 120 by a channel-formed plate-shaped member 410, and the detecting device 130 by a detecting device 420.

The channel-formed plate-shaped member 410 is comprised of the channel-formed plate-shaped member 120 appearing in FIG. 1, a gradient index rod lens 411 having the same shape, the same size, and the same characteristics as those of the gradient index rod lens 101 appearing in FIG. 1, and two pins 412.

The gradient index rod lens 411 has an exit-side surface thereof fixed to the surface 121a of the upper glass substrate 121 opposite to the middle glass substrate 122 such that the exciting light and the detecting light exiting from the gradient index rod lens 411 are perpendicularly incident on each of the upper glass substrate 121, the middle glass substrate 122, and the lower glass substrate 123 to enter the channel 124.

The detecting device 420 is disposed under the channel-formed plate-shaped member 410, and is comprised of a wavelength filter 421 identical to the wavelength filter 131 of the microchemical system 10 shown in FIG. 1, a photoelectric converter 422 identical to the photoelectric converter 132 of the microchemical system 10 shown in FIG. 1, and a computer 424 which is identical to the computer 134 of the microchemical system 10 shown in FIG. 1 and is connected to the photoelectric converter 422 via a lock-in amplifier 423 identical to the lock-in amplifier 133 of the microchemical system 10 shown in FIG. 1.

The wavelength filter 421 has one surface thereof attached to the surface of the lower glass substrate 123 in a position facing toward the channel 124 of the channel-formed plate-shaped member 410, and the photoelectric converter 422 has one surface thereof attached to the other surface of the wavelength filter 421 in a position facing toward the channel 124.

The pins 412 are erected at symmetrical locations with respect to the gradient index rod lens 411.

The stopper-equipped optical fiber 400 is comprised of an optical fiber 405 connected to the two-wavelength multiplexing device 115, and a stopper 401 (annular member) fixed to the leading end of the optical fiber 405. The stopper 401 is comprised of a collar 401a fixed to the optical fiber 405, and an annular part 401b formed integrally with the periphery of the collar 401a. The annular part 401b has two holes 402 formed in a surface thereof opposed to the upper glass substrate 121, for receiving the two pins 412 therein. Further, the annular part 401b has through holes 403 formed in the outer peripheral surface thereof such that the through holes 403 extend to the respective holes 402 perpendicularly thereto toward the longitudinal central axis of the stopper 401. Check pins 404 which can be fitted in the through holes 403 are removably attached thereto. The optical fiber 405 has the same characteristics as those of the optical fiber 102 of the microchemical system 10 shown in FIG. 1.

In the stopper-equipped optical fiber 400 and the channel-formed plate-shaped member 410, the pins 412 are received in the holes 402 of the stopper 401, whereby the stopper 401 and the channel-formed plate-shaped member 410 are integrally joined with each other to connect the optical fiber 405 and the gradient index rod lens 411 such that their optical axes are aligned with each other. Further, when the stopper 401 and the channel-formed plate-shaped member 410 are thus integrated with each other, the pins 412 may be fixed to the holes 402 by fitting the check pins 404 in the through holes 403 formed in the outer peripheral surface of the annular part 401b of the stopper 401. The stopper 401 and the channel-formed plate-shaped member 410 can be thus integrally fixed to each other such that the stopper 401 and the channel-formed plate-shaped member 410 cannot be separated from each other unless attempted intentionally.

The optical axis of the optical fiber 405 and the optical axis of the gradient index rod lens 411 are made more precisely aligned with each other by forming the holes 402 of the stopper 401 and the pins 412 such that they have as equal diameters as possible. Further, they can be more precisely aligned with each other by increasing the number of holes 402 and the number of associated pins 412.

According to the microchemical system 40 shown in FIG. 4, there is not used any component in direct contact with the gradient index rod lens 411, so that there is less possibility of the gradient index rod lens 411 being flawed or chipped, to thereby prevent such a flaw or chip from affecting the lens characteristics of the gradient index rod lens 411. As a result, it is possible to increase the number of times of use of the channel-formed plate-shaped member 410 to which is fixed the gradient index rod lens 411, and this makes it possible to reduce the running cost of the microchemical system 40 and perform precise analysis enhanced in reproducibility.

According to the microchemical system 40 shown in FIG. 4, the photoelectrical converter 422 of the detecting device 420 is fixed to the channel-formed plate-shaped member 410. As a result, it is not necessary to adjust the position of the photoelectrical converter 422 each time detection is performed, and hence it is possible to improve the working efficiency of the user. Since predetermined jigs for adjustment of the position can be dispensed with, it is possible to reduce the size of the microchemical system. Further, since the position of the photoelectrical converter 422 does not change each time detection is performed, it is possible to perform precise analysis enhanced in reproducibility.

The shapes of the stopper 401, the holes 402, and the pins 412 used in the microchemical system 40 shown in FIG. 4 are not limited to those described above.

Although the wavelength filter 131 and the photoelectrical converter 132 used in the microchemical system 10 shown in FIG. 1, the microchemical system 20 shown in FIG. 2, and the microchemical system 30 shown in FIG. 3 are not fixed to the lower glass substrate 123 of the respective channel-formed plate-shaped members 120, 210, and 310, this is not limitative, but they may be fixed to the lower glass substrate 123 of the respective channel-formed plate-shaped members 120, 210, and 310.

Although the upper glass substrate 121, the middle glass substrate 122, and the lower glass substrate 123 of the channel-formed plate-shaped member 120 of the microchemical system 10 shown in FIG. 1, the channel-formed plate-shaped member 210 of the microchemical system 20 shown in FIG. 2, the channel-formed plate-shaped member 310 of the microchemical system 30 shown in FIG. 3, and the channel-formed plate-shaped member 410 of the microchemical system 40 shown in FIG. 4 are made of a glass, the present invention is not limited to this specific example.

INDUSTRIAL APPLICABILITY

As described in detail above, according to the microchemical system according of the present invention, the optical fiber can be removably connected using a joint part. Therefore, in the cases of the channel having been stained, the channel-formed plate-shaped member having been broken, and the optical fiber having been broken, by replacing only the channel-formed plate-shaped member to which the converging lens is fixed, it is possible to perform fine and precise detection by suppressing contamination of the liquid-borne sample and reduce the running cost of the microchemical system.

According to the microchemical system of the present invention, the joint part is a connector provided midway of the optical fiber. As a result, the exciting light source and the detecting light source can be easily connected to and disconnected from the converging lens.

According to the microchemical system of the present invention, the joint part is an FC connector provided midway of the optical fiber. As a result, the exciting light source and the detecting light source can be easily connected to and disconnected from the converging lens. Further, the connection can be made solid, and hence there is less loss in the amount of the exciting light and the detecting light propagating through the optical fiber.

According to the microchemical system of the present invention, the joint part is provided at an end of the optical fiber opposed to the converging lens via which the optical fiber is connected to the converging lens. As a result, the construction of the joint part can be made simple, whereby the microchemical system can be made smaller in size.

According to the microchemical system of the present invention, the joint part can be removably attached to the converging lens. As a result, the construction of the joint part can be made yet simpler, whereby the microchemical system can be made yet smaller in size.

According to the microchemical system of the present invention, the joint part comprises an annular member that can be fitted on the converging lens. As a result, the construction of the joint part can be made yet simpler, whereby the microchemical system can be made yet smaller in size.

According to the microchemical system of the present invention, the joint part can be removably attached to the channel-formed plate-shaped member. As a result, the construction of the joint part can be made yet simpler, whereby the microchemical system can be made yet smaller in size.

According to the microchemical system of the present invention, the joint part is configured such that the first annular member can be fitted on the converging lens, and the second annular member fixed to the first annular member in a manner coaxially accommodating the first annular member therein has the annular protruding part formed on the inner peripheral surface thereof, for being fitted in the annular groove formed in the outer peripheral surface of the third annular member fixed to the channel-formed plate-shaped member in a manner coaxially accommodating the converging lens therein. As a result, the construction of the joint part can be made yet simpler, whereby the microchemical system can be made yet smaller in size.

According to the microchemical system of the present invention, the joint part is configured such that the annular member has holes formed in the end face thereof opposed to the channel-formed plate-shaped member, for receiving the pins erected at symmetric locations with respect to the converging lens. As a result, the construction of the joint part can be made yet simpler, whereby the microchemical system can be made yet smaller in size.

According to the microchemical system of the present invention, the joint part enables connection between the exciting light source and the detecting light source, and the converging lens, in a manner such that the optical axis of the converging lens and the optical axis of the optical fiber are coaxial with each other. As a result, jigs for aligning the optical axes of the exciting light and the detecting light are made unnecessary, so that the construction of the joint part can be made yet simpler, whereby the microchemical system can be made yet smaller in size.

According to the microchemical system of the present invention, the frequency of the exciting light is different from that of the detecting light, and the converging lens has chromatic aberration. As a result, the focal positions of the exciting light and the detecting light can be shifted from one another without using any external optical systems, whereby the microchemical system can be made yet smaller in size.

According to the microchemical system of the present invention, the converging lens has chromatic aberration. As a result, the focal positions of the exciting light and the detecting light can be positively shifted from one another without using any external optical systems.

According to the microchemical system of the present invention, the converging lens is a gradient index lens. As a result, the converging lens can be made smaller in size, whereby the microchemical system can be made yet smaller in size.

According to the microchemical system of the present invention, the gradient index lens is a rod lens having a cylindrical shape. As a result, the gradient index lens can be easily held, and the optical axes of the optical fiber and the gradient index lens can be easily aligned with each other.

According to the microchemical system of the present invention, the channel-shaped plate-formed member is made of a glass. As a result, the channel-shaped plate-formed member has high resistance to chemicals, whereby the detecting accuracy of the microchemical system can be improved.

According to the microchemical system of the present invention, the optical fiber propagates the exciting light and the detecting light with a single mode. As a result, the thermal lens formed by the exciting light can be made smaller in size with little aberration, and hence more precise detection can be carried out.

According to the microchemical system of the present invention, the detecting means is fixed on a surface of the channel-formed plate-shaped member, opposite to the converging lens fixed thereto, in a position facing toward the channel of the channel-formed plate-shaped member. As a result, the adjustment of the positions of the converging lens and the detecting means can be made unnecessary, and moreover, since jigs for the adjustment are unnecessary, the microchemical system can be made yet smaller in size, and further the positioning of the converging lens and the detecting means with respect to the channel can be more reliably carried out each time analysis of a sample is carried out, whereby the microchemical system can perform detection with enhanced reproducibility and increased precision.

The invention claimed is:

1. A microchemical system comprising a channel-formed plate-shaped member that is equipped with a channel for containing a sample, an exciting light source that irradiates exciting light onto the sample via a converging lens, a detecting light source that irradiates, via the converging lens, detecting light onto a thermal lens formed within the sample by the irradiated exciting light, and detecting means for detecting the irradiated detecting light via the formed thermal lens, wherein the exciting light source and the detecting light source are connected to the converging lens via an optical fiber for propagating the exciting light and the detecting light to the converging lens, wherein the converging lens is fixed to the channel-formed plate-shaped member, the optical fiber has a joint part capable of disconnecting the exciting light source and the detecting light source from the converging lens, and the detecting means is provided in a position opposite to the converging lens.

2. A microchemical system as claimed in claim 1, wherein said joint part comprises a connector provided midway along the optical fiber.

3. A microchemical system as claimed in claim 2, wherein said joint part comprises an FC connector.

4. A microchemical system as claimed in claim 1, wherein said joint part is provided at an end of the optical fiber via which the optical fiber is connected to the converging lens.

5. A microchemical system as claimed in claim 4, wherein said joint part is removably attachable to the converging lens.

6. A microchemical system as claimed in claim 5, wherein said joint part comprises an annular member adapted to be fitted on the converging lens.

7. A microchemical system as claimed in claim 4, wherein said joint part is removably attachable to the channel-formed plate-shaped member.

8. A microchemical system as claimed in claim 7, wherein said joint part comprises a first annular member adapted to be fitted on the converging lens, a second annular member that is fixed to said first annular member in a manner coaxially accommodating said first annular member therein and that has an annular protruding part formed on an inner peripheral surface thereof, and a third annular member that is fixed to the channel-formed plate-shaped member in a manner coaxially accommodating the converging lens therein and that has an annular groove formed in an outer peripheral surface thereof, for receiving said annular protruding part.

9. A microchemical system as claimed in claim 7, wherein said joint part comprises pins erected at symmetrical locations with respect to the converging lens, and an annular member that is coaxially fixed to the optical fiber and that has holes formed in an end face thereof which is opposed to the channel-formed plate-shaped member.

10. A microchemical system as claimed in claim 1, wherein said joint part enables connection between the exciting light source and the detecting light source, and the converging lens, in a manner such that an optical axis of the converging lens and an optical axis of the optical fiber are coaxial with each other.

11. A microchemical system as claimed in claim 1, wherein a frequency of the exciting light is different from that of the detecting light.

12. A microchemical system as claimed in claim 1, wherein the converging lens has chromatic aberration.

13. A microchemical system as claimed in claim 1, wherein the converging lens comprises a gradient index lens.

14. A microchemical system as claimed in claim 13, wherein the gradient index lens comprises a rod lens having a cylindrical shape.

15. A microchemical system as claimed in claim 1, wherein the channel-shaped plate-formed member is made of a glass.

16. A microchemical system as claimed in claim 1, wherein the optical fiber propagates the exciting light and the detecting light to the converging lens with a single mode.

17. A microchemical system as claimed in claim 1, wherein the detecting means is fixed on a surface of the channel-formed plate-shaped member, opposite to the converging lens fixed thereto, at a location facing toward the channel of the channel-formed plateshaped member.

18. A microchemical system comprising a channel-formed plate-shaped member that is equipped with a channel for containing a sample, an exciting light source that irradiates exciting light onto the sample via a converging lens, a detecting light source that irradiates, via the converging lens, detecting light onto a thermal lens formed within the sample by the irradiated exciting light, and detecting means for detecting the irradiated detecting light via the formed thermal lens, wherein the exciting light source and the detecting light source are connected to the converging lens via an optical fiber for propagating the exciting light and the detecting light to the converging lens, wherein the converging lens is fixed to the channel-formed plate-shaped member, and the optical fiber has a joint part capable of disconnecting the exciting light source and the detecting light source from the converging lens; and wherein said joint part comprises an annular member adapted to be fitted on the converging lens, and said joint part is removably attachable to the converging lens via said annular member.

19. A microchemical system comprising a channel-formed plate-shaped member that is equipped with a channel for containing a sample, an exciting light source that irradiates exciting light onto the sample via a converging lens, a detecting light source that irradiates, via the converging lens, detecting light onto a thermal lens formed within the sample by the irradiated exciting light, and detecting means for detecting the irradiated detecting light via the formed thermal lens, wherein the exciting light source and the detecting light source are connected to the converging lens via an optical fiber for propagating the exciting light and the detecting light to the converging lens, wherein the converging lens is fixed to the channel-formed plate-shaped member, and the optical fiber has a joint part capable of disconnecting the exciting light source and the detecting light source from the converging lens;

wherein said joint part comprises a first annular member adapted to be fitted on the converging lens, a second annular member that is fixed to said first annular member in a manner coaxially accommodating said first annular member therein and that has an annular protruding part formed on an inner peripheral surface thereof, and a third annular member that is fixed to the channel-formed plate-shaped member in a manner coaxially accommodating the converging lens therein and that has an annular groove formed in an outer peripheral surface thereof, for receiving said annular protruding part; and wherein said joint part is removably attachable to the channel-formed plate-shaped member via said second annular member and said third annular member.

20. A microchemical system including a channel-formed plate-shaped member that is equipped with a channel for containing a sample, an exciting light source that irradiates exciting light onto the sample via a converging lens, a detecting light source that irradiates, via the converging lens, detecting light onto a thermal lens toned within the sample by the irradiated exciting light, and detecting means for detecting the irradiated detecting light via the formed thermal lens, wherein the exciting light source and the detecting light source are connected to the converging lens via an optical fiber for propagating the exciting light and the detecting light to the converging lens, wherein the converging lens is fixed to the channel-formed plate-shaped member, and the optical fiber has a joint part capable of disconnecting the exciting light source and the detecting light source from the converging lens;

wherein said joint part comprises pins erected at symmetrical locations with respect to the converging lens, and an annular member that is coaxially fixed to the optical fiber and has holes for receiving said pins formed in an end face thereof which is opposed to the channel-formed plate-shaped member; and wherein said joint part is removably attachable to the channel-formed plate-shaped member via said pins and said annular member.

\* \* \* \* \*